US010330533B2

(12) United States Patent
Kaishatsu (10) Patent No.: US 10,330,533 B2
(45) Date of Patent: Jun. 25, 2019

(54) EMISSION SPECTROSCOPIC ANALYZER (71) Applicant: SHIMADZU CORPORATION, Nakagyo-ku, Kyoto-shi (JP)

(72) Inventor: Tatsuya Kaishatsu, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/903,197

(22) Filed: Feb. 23, 2018

(65) Prior Publication Data

US 2018/0238736 A1 Aug. 23, 2018

(30) Foreign Application Priority Data

Feb. 23, 2017 (JP) .................................. 2017-032209

(51) Int. Cl.
| | |
|---|---|
| *G01J 3/30* | (2006.01) |
| *G01J 3/443* | (2006.01) |
| *G01J 3/28* | (2006.01) |
| *G01J 3/02* | (2006.01) |
| G01N 21/67 | (2006.01) |
| G01N 21/27 | (2006.01) |

(52) U.S. Cl.
CPC ............... *G01J 3/443* (2013.01); *G01J 3/027* (2013.01); *G01J 3/28* (2013.01); *G01J 2003/2879* (2013.01); *G01N 21/274* (2013.01); *G01N 21/67* (2013.01)

(58) Field of Classification Search
CPC ......... G01J 3/443; G01N 21/67; G01N 21/69; G01N 21/3103; G01N 21/62

USPC ......................................................... 356/311
See application file for complete search history.

(56) References Cited

U.S. PATENT DOCUMENTS

| | | | | |
|---|---|---|---|---|
| 6,915,704 B2* | 7/2005 | Umekage | .................. | G01F 1/66 702/45 |
| 2004/0261539 A1* | 12/2004 | Umekage | .................. | G01F 1/66 73/861.27 |

FOREIGN PATENT DOCUMENTS

JP     2001083096     3/2001

* cited by examiner

*Primary Examiner* — Md M Rahman
(74) *Attorney, Agent, or Firm* — Andrew F. Young, Esq.; Lackenbach Siegel, LLP (57) ABSTRACT

An emission spectroscopy instrumentation is easily operated and includes a calculation element 154 that calculates a variation of the measurement values of every detector relative to a plurality of measurements of a standard; a determination element 155 that determines whether any an additional measurement is required when a variation relative to all detectors is within an acceptable value and an addition measurement is required when a variation relative to any one detector is out of an acceptable value; a notification element 156 that notifies to an operator a determination result according to the determination element 155, and a calculation-determination control element 153 that controls the calculation element 154 and the determination element 155 that calculates the variation and makes a determination at the timing when the measurement of the standard sample is executed at predetermined times, and calculates a variation and makes a determination at every one additional measurement when the additional measurement is needed.

20 Claims, 8 Drawing Sheets

FIG. 1A

Spectroscopic Element 120

FIG. 1B

Excitation Element 110

FIG. 1C

Control-Processing Element — 130

EMISSION SPECTROSCOPIC ANALYZER

CROSS REFERENCE TO RELATED APPLICATIONS

This application relates to, and claims priority from, JP 2017-032209 filed Feb. 23, 2017, the entire contents of which are incorporated herein by reference.

FIGURE SELECTED FOR PUBLICATION

FIG. 2

BACKGROUND OF THE INVENTION

Field of the Invention

The present invention relates to an emission spectroscopy instrumentation (emission spectroscopy) that excites a sample to emit light and measures spectroscopically the emitted light.

Description of the Related Art

Generally, an emission spectroscopy excites the instant sample to vaporize and emit light by providing a solid sample, such as a metal or non-metal with an energy generated by e.g., an arc discharge or a spark discharge, induces the emission light into a spectroscopy, and extracts and detects the spectral line due to the specific wavelength of each element (e.g., refer to the Patent Document 1). Particularly, the emission spectroscopy that applies the spark discharge as an excitation source can provide a highly accurate analysis so that such emission spectroscopy is widely used, for example, in the factory for steel and non-ferrous metal to carry out a composition analysis of the produced metal.

As disclosed in the Patent Document 1, a spectroscope (spectral device) of such emission spectroscopy includes a diffraction grating that performs wavelength dispersion of light from a sample, a slit that is in-place at the location to which the spectral line of each wavelength reaches, and a plurality of photodetectors (normally, photomultiplier) that detects the light that passes through each slit, so that the spectral line of each inherent wavelength for a plurality of elements is obtained. In addition, nowadays, instead of the above slit or photodetector, a spectroscope having a system that consists of a plurality of multi-channel-type photodetectors such as linear CCD sensors having many light receiving elements is widely used. The emission spectroscopy having the spectroscope using such system detects lights, having a predetermined wavelength range among the light subjected to the wavelength dispersion at the diffraction grating, by the multi-channel-type photodetectors at once.

Relative to such emission spectroscopy, a calibration work is generally carried out upon a measurement using a standard sample to ensure the accuracy of the measurement. During the calibration work, first, the standard sample containing a predetermined concentration of the target element is subjected to an excited emission, and, at that time, a deviation of the measurement value of the receiving light strength according to the photodetector from the standard value is examined and the calibration data (e.g., calibration coefficient and so forth) to compensate such deviation is obtained. In addition, a default value that is set up at the stage, for example, when the emission spectroscopy is delivered to the user, is used. Such above calibration data are acquired every element (or spectral line) that is a detection target and stored in the storing device such as a memory and so forth. And, since then, when the sample containing an unknown concentration of the target element is measured, the calibration data relative to the target element (or spectral line) is read out from the storing device, so that the measurement value of the signal intensity obtained by the measurement of the target sample is compensated using the calibration data.

In addition, relative to the emission spectroscopy, according to the system in which, as set forth above, the spectral line is detected by the multi-channel-type photodetector, the distance between each structural element that consists of the spectroscope changes due to the analysis environment (typically temperature), so that an incident location of each spectral line on the light receiving surface of the photodetector varies along with such distance change. Specifically, a deviation of the corresponding relationship between each light receiving element that are arranged on the light receiving surface of the multi-channel-type photodetector and the light wavelength that the light receiving element detects occurs.

Therefore, the emission spectroscopy, according to such system, carries out the calibration of the detection wavelength by each light receiving element (hereinafter wavelength calibration) in addition to the calibration of the sensitivity of the detector (detector sensitivity). Specifically, first, the standard sample containing the target element is measured, and the incident location of the spectral line of the target element on the light receiving surface of the detector is identified according to the intensity of the light that each light receiving element included in the multi-channel-type photodetector receives. The identification of such incident location is carried out relative to e.g., the two spectral lines (of known wavelength) that are incident into the location on the light receiving surface as much as far away, and the light wavelength incident to each location (i.e., each light receiving element) of the light receiving surface can be identified based on the wavelength of each spectral line and the incident location thereof. The data of the corresponding relationship between such light receiving element and the wavelength of the incident light are acquired for each of a plurality of multi-channel-type detectors installed to the spectroscope and stored in the storing device such as a memory as the wavelength calibration data, which are used for the following measurement.

RELATED PRIOR ART DOCUMENTS

Patent Document

Patent Document 1: JP Patent Published 2001-83096 A1

ASPECTS AND SUMMARY OF THE INVENTION

Objects to be Solved

The above emission spectroscopy carries out repeatedly the measurement of the standard sample for one-time calibration work, and when the operator determines that the measurement value is stable (constant), the measurement of the standard sample ends and the calibration data such as the calibration coefficient and so forth are calculated. However, when the measurement of the standard sample ends before the measurement value is satisfactorily constant, no adequate calibration data can be acquired. On the other hand, when many measurements of the standard sample are carried out more than needed, the time and the financial burden for such calibration work increase. Particularly, with regard to the solid emission spectroscopy that excites a solid sample by discharge, the discharge room is purged with argon gas upon measurement, so that the more the measurement is carried out, the more the expensive argon gas is consumed. Regardless, the benchmark for the measurement end timing determined by the operator is ambiguous, so that it is very difficult that only the adequate number of the measurements of the standard sample is carried out unless the operator is well trained.

The present invention is carried out considering such circumstance, and a purpose of the present invention is to provide an inexperienced operator with an emission spectroscopy that allows such operator to carry out the adequate number of measurements of the standard sample for the calibration.

Means for Solving the Problem

For solving above problem, an emission spectroscopy, according to the present invention, is the emission spectroscopy, which excites a sample (material) and emits light and detects a plurality of spectral lines obtained by wavelength dispersion of the emission light by a plurality of detectors, comprises:

(a) a calculation means that calculates variation of measurement values obtained by multiple measurements of a standard sample relative to each of the plurality of the detectors;

(b) a determination means that determines that no additional measurement is required when the variation relative to all of the plurality of detectors is within a predetermined acceptable value and an additional measurement is required when the variation relative to at least one of the plurality of detectors is out of the acceptable value;

(c) a notification means that notifies a determination results by the determination means to an operator;

(d) a control means that controls the calculation means and the determination means so that the calculation means calculates the variation and the determination means determines at a timing when the measurement of the standard sample is carried out predetermined times, and when the determination means determines that the additional measurement is required, since then, the calculation means calculates the variation and the determination means determines every time one additional measurement is carried out.

Now the calculation means calculates, for example, a standard deviation, a dispersion coefficient or a variation coefficient and so forth, but not limited thereto.

The emission spectroscopy, according to the above aspect, calculates the variation of the measurement values by the calculation means at the timing when the standard sample is measured predetermined times (e.g., 3 times) during the calibration work. And the determination means determines whether the variation is within the acceptable value or not, and based on the result thereof, the determination means determines necessity of the additional measurement. Then when it is determined that the variation of the measurement value is satisfactorily small relative to all detectors so that no additional measurement is needed (i.e., all detectors meet the measurement condition), the notification means notifies such determination to the operator. On the other hand, even when it is determined that the variation of the measurement value (measurement value variation) relative to at least one detector is large so that the additional measurement is needed, the notification means notifies such determination to the operator, so that the operator can carry out the additional measurement of the standard sample using the emission spectroscopy. Subsequently, the calculation means calculates the variation and the determination means determines every measurement of the standard sample (additional measurement), the determination result is notified to the operator. Therefore, the operator can end the calibration work right after the timing when the measurement value becomes constant (stable). As a result, the incident of that the measurement of the standard sample ends before the measurement value becomes constant, or that the measurement of the standard sample continues repeatedly even after the measurement value is constant, can be prevented.

However, given the calculation means calculates the variations based on all measurement values obtained from the beginning of the measurement of the standard sample to the update measurement, it may take a long time until the variation settles within the acceptable value.

Accordingly, the calculation means of the present invention calculate the variation based on the measurement values of the predetermined number (of the standard samples) among the measurement values that are obtained by multiple measurements of the standard sample, and it is preferable that the predetermined number of the measurement values is selected to provide the minimum variation value.

Figure 7:
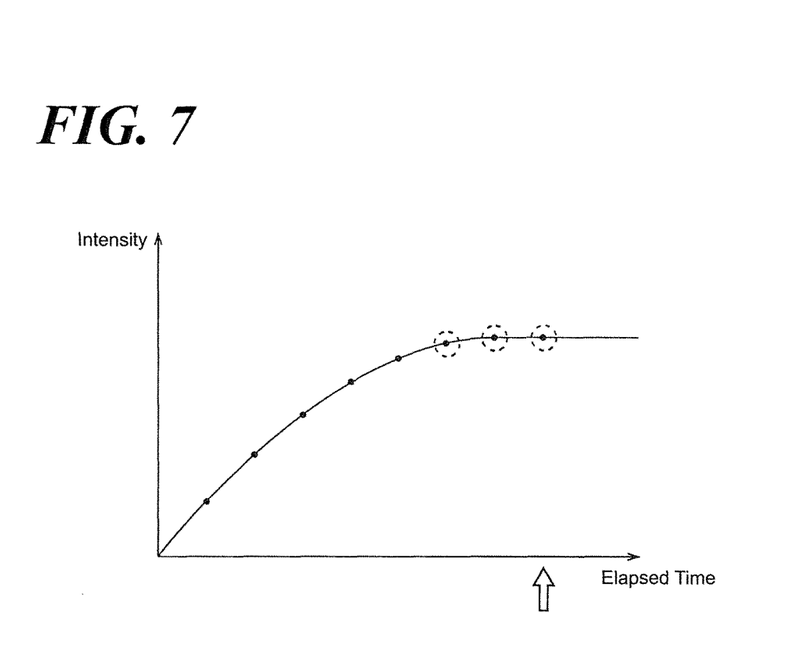
FIG. 7 is a graph illustrating the variation of the intensity of the spectral line according to one example.
Figure 8:
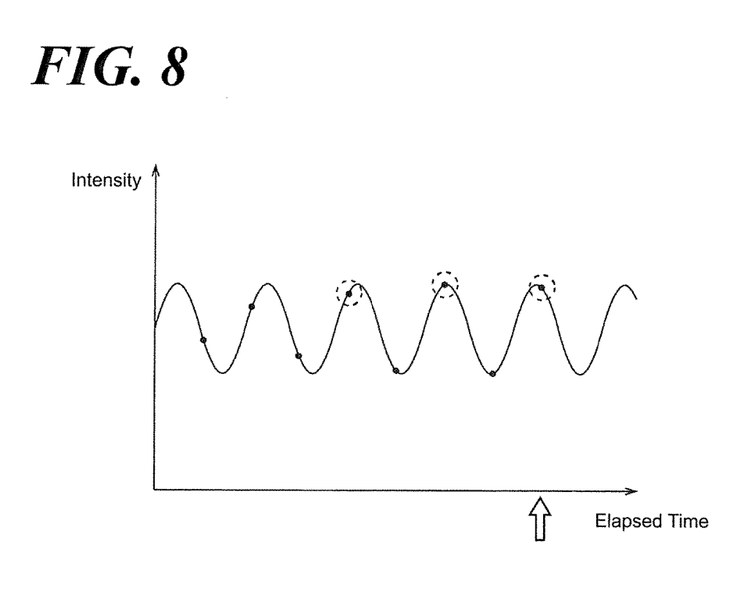
FIG. 8 is a graph illustrating the variation of the intensity of the spectral line according to another example.

Referring to FIG. 7, FIG. 8, the inventor sets forth in detail the determination whether an additional measurement is needed or not based on the variation calculation and the calculation result thereof. In addition, here, it is given that the "predetermined number of times" is "3 times" relative to the control means and the "predetermined number of pieces" is "3 pieces" relative to the calculation means.

FIG. 7, FIG. 8 are schematic views illustrating the time variation of the intensity of a spectral line following the beginning of the calibration work, and the black circle in FIG. denotes the timing and the light receiving intensity of the detector corresponding to the spectral line thereof when the measurement is carried out. Further, the upwards thick arrow denotes the timing when the variation value of the 3 measurement values is within the acceptable value when the predetermined number (3, this time) of the measurement values is selected so that the variation value becomes minimum, and the black circle surrounded with the broken line in FIG, denotes the selected 3 measurement values. In addition, for convenience sake, the measurements are carried out in the constant time interval, but the actual measurement time interval may not always be constant.

Now, referring to FIG. 7, when the intensity of the spectral line corresponding to a detector varies in one direction (the direction in which the intensity increases in such example) with time and converges over time and given 3 (three) measurement values are selected to provide the minimum standard deviation every additional measurement (here, following the 4th measurement), the most recent 3 measurement values are always applied to determination. And when the standard deviation of the 3 measurement values is within the acceptable value at the timing when the intensity of the spectral converges on some constant level (the timing denoted by the thick arrow in FIG.), it is determined that the measurement end condition relative to the detector meets the requirements.

On the other hand, referring to FIG. 8, when the intensity of the spectral line of the detector corresponding to a detector oscillates with time in the constant amplitude and does not converge, even if the most recent 3 measurement values are selected, the standard deviation may not be minimum always. Regardless, once the standard deviation of the most recent 1 (the last) measurement value and any two of measurement values obtained from the beginning to the present (any before the last) are within the acceptable value, it is determined that the measurement end condition relative to the instant detector meets the requirements at that timing (denoted by the thick arrow in FIG.).

In addition, it is preferable that the emission spectroscopy of the present invention further comprises an additional measurement execution means, in addition to or instead of the notification means, which executes an additional measurement of the standard sample when the determination means determines that the additional measurement of the standard sample is needed.

In addition, according to the present invention, the "measurement value" used for calculation of the variation is typically the light receiving intensity of the detector, but in addition, for example, a calibration coefficient to calibrate the deviation between the light receiving intensity and the predetermined benchmark value is calculated, and such calibration coefficient can be applied to the "measurement value" that is applied to calculate the variation. In addition, when the detector is a multi-channel-type detector, the "measurement value" that is applied to calculate the variation can be also specified as the incident location of the predetermined spectral line on the light receiving surface of the multi-channel-type detector.

In addition, according to the emission spectroscopy of the present invention, it is further preferable that the determination means determines that the calibration is erroneous when the variation relative to at least one of the plurality of detectors is more than the acceptable value despite execution of the measurement of the standard sample over the predetermined maximum number of times.

Effect of the Invention

As set forth above, according to the emission spectroscopy of the present invention, even an inexperienced operator can carry out an adequate number of the measurement of the standard sample for calibration.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Hereafter, referring to FIGs, the inventor illustrates the best mode of Embodiment of the present invention.

Embodiment

Figure 1A:
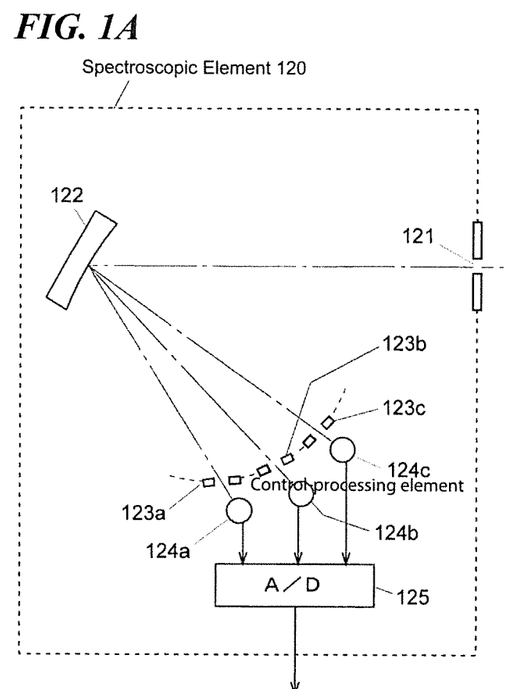
FIGS. 1A-1C are schematic diagrams illustrating an emission spectroscopy according to the aspect of the Embodiment 1 of the present invention.
Figure 1B:
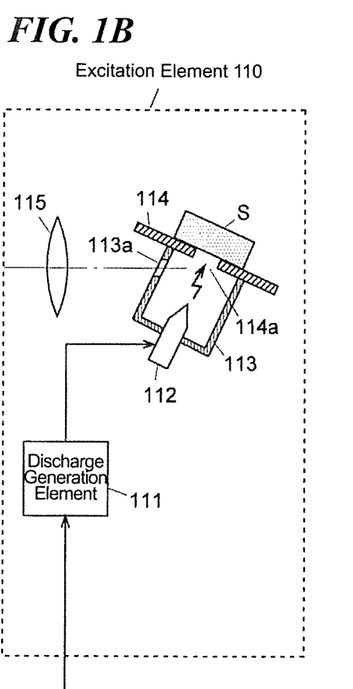
Figure 1C:
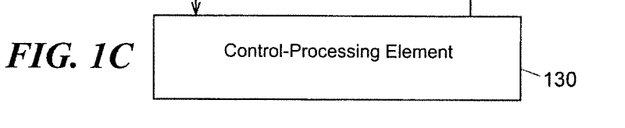

FIGS. 1A-1C are schematic diagrams illustrating an emission spectroscopy according to the aspect of the Embodiment 1 of the present invention. The emission spectroscopy, according to the aspect of the present invention, comprises an excitation element 110 that excites the solid sample to emit light, a spectroscopic element 120 that subjects the emission light from the sample to wavelength dispersion, and a control-and-processing element 130 that controls each element and executes a data processing.

The excitation element 110 further comprises a discharge generation element 111, an electrode bar 112, a discharge chamber 113, a sample loading plate 114 and a converging lens 115. The discharge chamber 113 comprises an analysis opening that opens obliquely upward and a light induction hole 113a that induces the light from the discharge chamber, a sample loading plate 114 is attachably and detachably mounted to the superior portion of the discharge chamber 113 as covering the analysis opening. The sample loading plate 114 comprises a central opening 114a that is smaller than a size of the sample S, the sample S is loaded on the sample loading plate 114 as covering the central opening 114a so that a part of the bottom surface (subjected surface to the analysis) of the sample S is exposed to the inside of the discharge chamber 113. An electrode bar 112, of which tip faces the central opening 114a, for discharge is installed inside the discharge chamber 113.

The discharge generation element 111 adds pulse-like high-voltage to the electrode bar 112 in synchronism with the predetermined frequency (e.g., 400 Hz). When analyzing the sample S, the gas induction mechanism, not shown in FIG., induces the argon gas into the inside of the discharge chamber 113, and the sample S, such as iron or non-ferrous metal and so forth, excites and emits light by a spark discharge from the electrode bar 112 under argon gas atmosphere. Such emission light passes through the light induction hole 113a installed to the discharge chamber 113 and is converged by the converging lens 115 and induced into the spectroscopic element 120.

The spectroscopic element 120 comprises an entrance slit 121, a diffraction grating 122, exit slits 123a, 123b, 123c installed side by side on the Rowland circle, detectors 124a, 124b, 124c that are photoelectron multipliers. Such spectroscopic element 120 is a so-called Paschen-Runge spectrometer. Each of the exit slits 123a, 123b, 123c and the detectors 124a, 124b, 124c is in-place to detect the spectral line having an inherent wavelength to each specific element among lights having each wavelength that the diffraction grating 122 disperses. For example, each of detectors 124a, 124b, 124c is in-place at the location at which the spectral lines of carbon (C), silicon (Si) and Mn (manganese) are detected. Needless to say, actually, not only such three elements, but also the system can detect the spectral line of other elements as many as furthermore.

The detection signal from each of the detectors 124a, 124b, 124c is input to the control-processing element 130 via the A/D converter 125, and then the predetermined data processing is executed, so that the intensity of the spectral line of the specific element is acquired, and based on the intensity, a quantitative analysis relative to each element is executed.

Figure 2:
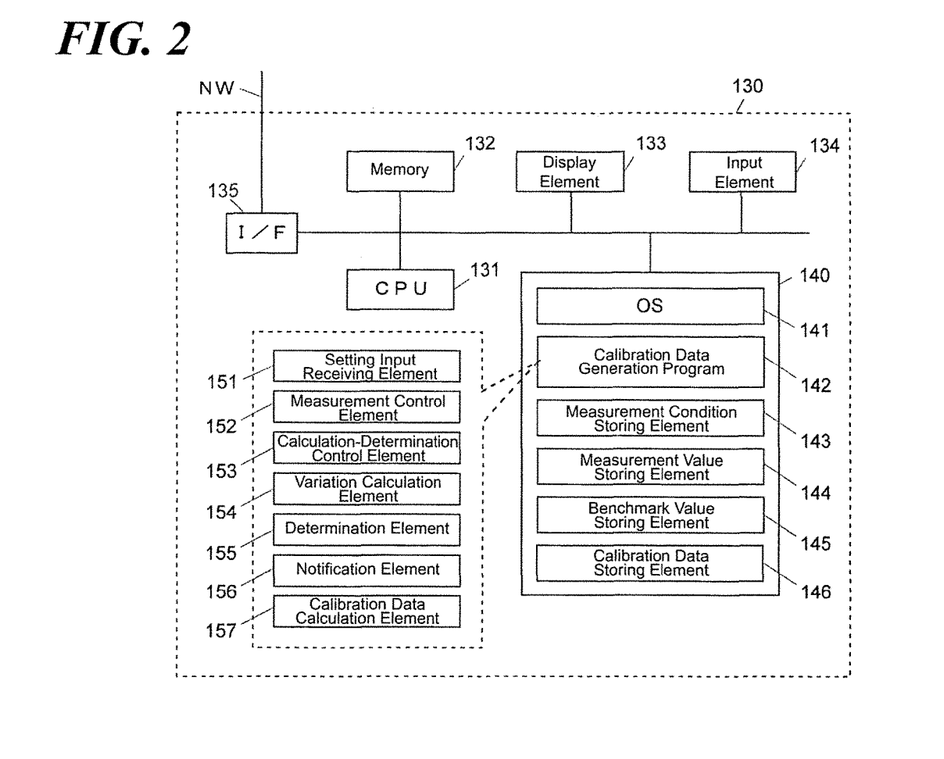
FIG. 2 is a block diagram illustrating a control and processing element according to the aspect of the same Embodiment.

Referring to FIG. 2, the actual aspect of the control-processing element 130 is such as a computer that comprises a CPU (central processing unit) 131 connecting a memory 132, a monitor consisting of LCD (liquid crystal display) and so forth, an input element 134 including a keyboard and a mouse and a memory storing element 140 consisting of a large memory unit including a HDD (hard disk drive) and a SSD (solid state drive) and so forth to one another. The memory element 140 comprises an OS (operating system) 141 and a calibration data generation program 142, and further comprises a measurement condition storing element 143, a measurement value storing element 144, a benchmark value storing element 145, and a calibration data storing element 146. The control-processing element 130 further comprises an interface (I/F) 135 that is operative to connect directly the outside devices and to the outside devices through a network such as a LAN (local area network) and connects the excitation element 110 and the spectroscopic element 120 through the network cable NW (or wireless LAN) from I/F 135.

Referring to FIG. 2, the calibration data generation program 142 associates with a setting input receiving element 151, a measurement control element 152, a variation calculation element 154, a determination element 155, a notification element 156, a calibration data calculation element 157, and a calculation-determination element 153 that controls the variation calculation element 154 and the determination element 155. Such elements are functional means that can be brought into reality by that the CPU 131 basically execute the calibration data generation program 142 by reading out into the memory 132 as a software. In addition, the calibration data generation program 142 is not mandatory to be a single program and can be integrated into the control program as a part to be operative to control the excitation element 110 and the spectroscopic element 120, but the aspect thereto is not limited.

Figure 3:
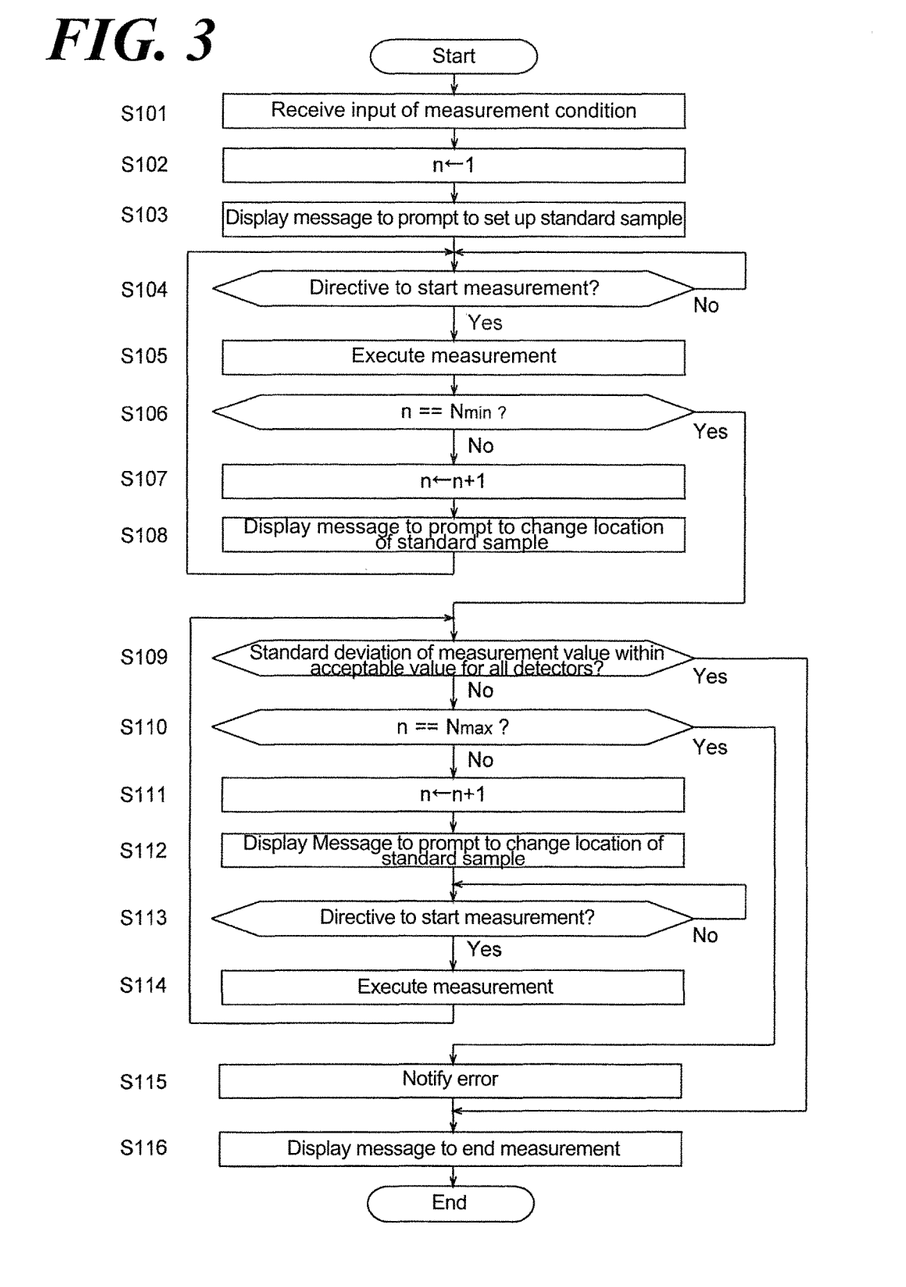
FIG. 3 is a flow-chart illustrating the measurement procedure of the standard sample for calibration according to the aspect of the same Embodiment.

Hereinafter, referring to the flow chart of FIG. 3, the inventor sets forth the calibration work procedure for the emission spectroscopy, according to the aspect of the present Embodiment, using the standard sample. First, the operator inputs the predetermined directive through the input element 134 to run the calibration data generation program 142. Then the setting receiving element 151 controls the display element 133 to display the predetermined input receiving page on the display element 133, so that operator can input a variety of the measurement conditions relative to the measurement of the standard sample (step S101). The measurement conditions to be input is, for example, the acceptable value of the measurement value, the minimum measurement times $N_{min}$ and the maximum measurement times $N_{max}$, and such input values are stored in the measurement condition storing element 143. In addition, the inventor sets forth the example in which the minimum measurement times $N_{min}$ is "3" and the maximum measurement times $N_{max}$ is "10".

Next, the calibration data generation program 142 specifies the variable n as 1 (step S102) and displays the message on the display element 133 to prompt the operator setting up the standard sample S in the excitation element 110 (step S103). Once the operator loads the standard sample S containing the predetermined concentration of the target element on the sample loading plate 114 of the excitation element 110 and directs starting the measurement through the input element 134, the measurement control element 152 controls the excitation element 110, so that the measurement of the standard sample S is executed (step S104, S105). Whereby, the spark discharge takes place from the electrode bar 112, so that the standard sample S is excited to emit light, and the emission light is subjected to dispersion at the spectroscopic element 120 and the detectors 124a, 124b, 124c detect the spectral lines of three elements (C, Si, Mn) therefrom. At this time, the signals acquired by the detectors 124a, 124b, 124c are sent to the control-processing element 130 via the A/D converter 125, and the intensity of the detection signal is stored in the measurement value storing element 144 as the measurement value relative to each detector 124a, 124b, 124c.

Once one measurement is completed, the calibration data generation program 142 determines whether the variable n is equal to the minimum measurement number $N_{min}$ or not (step S106), and if not equal, increments the variable n (step S107) and displays the message on the display element 133 to prompt changing the location of the standard sample S (step S108). The operator, who looks at the message, changes the location and the facing direction of the standard sample S on the sample loading plate 114, so that the area of the bottom surface of the standard sample S, which is different from the area already subjected to the measurement, is exposed from the central opening 114a of the sample loading plate 114. Then after, the step returns to the step S104 and the steps from the step S104 to the step S108 are repeatedly executed until the variable n becomes equal to the minimum measurement number at the step S106.

Then after, when the variable n is equal to the minimum measurement number $N_{min}$ at the step S106, i.e., the measurement of the standard sample S is executed three times, whether the standard deviation of the measurement values of the light receiving intensities obtained from the three measurements is within the acceptable value or not is determined (step S109). Specifically, firstly, the measurement values of each detector 124a, 124b, 124c of the three measurements of the standard sample S are read out from the measurement value storing element 144, and the variation calculation element 154 calculates the standard deviation of such measurement values every detector 124a, 124b, 124c. Next, the determination element 155 determines whether the value of the standard deviation relative to all detectors 124a, 124b, 124c is within the acceptable value that is specified at the step S101 or not.

And then, when all standard deviation relative to the detectors 124a, 124b, 124c are within the acceptable value, the notification element 156 displays the message denoting the completion of the measurement on the display element 133 (step S116) followed by the end of the measurement of the standard sample S.

On the other hand, when the standard deviation of the measurement values relative to any one of the detectors 124a, 124b, 124c is out of the acceptable value at the step S109, the calibration data generation program 142 determines whether the variable n is equal to the maximum measurement number $N_{max}$ or not (step S110), and if not equal, increments the variable n (step S111). And the notification element 156 displays the message on the display element 133 to prompt changing the location of the standard sample S (step 112). As well as set forth above, once the operator changes the location of the standard sample S and directs starting the measurement through the input element 134, the measurement control element 152 controls the excitation element 110, so that the measurement of the standard sample S is executed (steps S113, S114).

Then after, the step returns to the step S109 every time when the standard sample S is measured once and the variation calculation element 154 calculates the standard deviation and in addition, the determination element 155 determines whether the standard deviation is within the acceptable value or not. And until when it is determined that the values of the standard deviation relative to all detectors 124a, 124b, 124c are within the acceptable value at the step S109 (i.e., the measurement end condition relative to all detectors meets the requirement) (step S110), or until when the variable n is equal to the maximum measurement number $N_{max}$, the steps from the step S109 to the step S114 are repeatedly executed.

In addition, relative to the step S109, the variation calculation element 154 and the determination element 155 select the predetermined number. e.g., three, of measurement values from a plurality of measurement values obtained by that time to make the standard deviation thereof minimum by combination thereof and apply such standard deviation obtained by such combination to the determination. Specifically, when relative to any detector (any one of detectors 124a, 124b, 124c), the standard deviations relative to any three measurement values of a plurality of measurement values obtained from the first measurement to the nth (i.e., update) measurement are within the acceptable value, it is determined that the measurement end conditions relative to such detectors meet the requirement. In addition, the number of the selected measurement values is typically the same as the minimum measurement number $N_{min}$, but not limited thereto and any number more than 2 and less than n (the measurement number at that time) can be applied.

And then, the step proceeds to the step S116 when the measurement conditions relative to the detectors 124a, 124b, 124c meet requirements, and the notification element 156 displays the message denoting the completion of the measurement on the display element 133 followed by the end of the measurement of the standard sample.

In addition, when it is determined that the variable n is equal to the maximum measurement number $N_{max}$ at the step S110 (i.e., the standard sample is measured 10 times), the notification element 156 displays the message denoting the calibration error and ending the measurement on the display element 133 (steps S115, S116) and then the measurement of the standard sample S ends.

Accordingly, when the measurement of the standard sample S ends normally (i.e., end without a calibration error), the calibration data calculation element 157 calculates the calibration coefficient. Specifically, the measurement values obtained by the measurement of the standard sample S relative to each detector 124a, 124b, 124c (hereinafter called a "standard sample measurement value") and the benchmark value relative to each detector 124a, 124b, 124c, which is stored in the benchmark value storing element 145 in advance are read out to calculate the calibration coefficient to compensate the deviation between both values. At this time, for example, referring to FIG. 7 as set forth above, when the measurement values obtained by the measurement of the standard sample S converge, it is desirable that an average of the measurement values of the last few measurements (e.g., 3 measurements) is applied to calculate the calibration coefficient as the standard sample measurement value. In addition, for example, referring to FIG. 8 as set forth above, when the measurement values do not converge, it is desirable that an average of all measurement values obtained from the begging to the end of the measurement of the standard sample S is applied to calculate the calibration coefficient as the standard sample measurement value.

Here, for example, given the benchmark value that is stored in the benchmark value storing element 145 relative to the detector 124a is Ia1 and the standard sample measurement value obtained relative to the detector 124a is Ia2, the calibration coefficient Ka relative to the detector 124a is obtained by the following formula:

$$Ka=Ia1/Ia2$$

The calibration coefficients Kb, Kc relative to the other detectors 124b, 124c are obtained as well, and such calibration coefficients Ka, Kb, Kc are stored in the calibration data storing element 146. And, since then, when the sample containing an unknown concentration of the target element (here, C, Si, Mn) is measured, the calibration coefficient relative to the detector corresponding to the spectral line of the target element is read out from the calibration data storing element 146, so that the value of the signal intensity obtained by the measurement of the target sample is compensated using the calibration coefficient. For example, given the signal intensity of the detector 124a relative to the measurement of the target sample is $Ia_3$, the signal intensity value $Ia_3'$ following the compensation is represented in the formula below using the calibration coefficient stored in the calibration data storing element 146.

$$Ia_3'=Ka \times Ia_3$$

In addition, the above example sets forth one-point calibration when the intensity of the blank sample is zero, but the emission spectroscopy according to the aspect of the present Embodiment can accomplish the two points calibration.

Embodiment 2

Figure 4A:
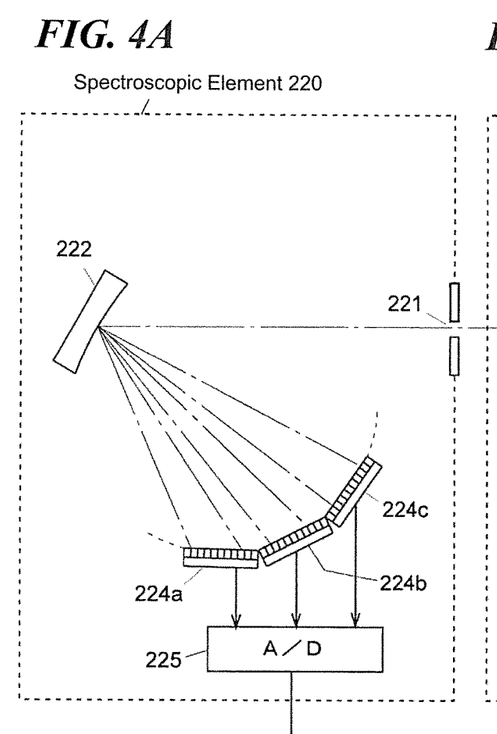
FIGS. 4A-4C are schematic diagrams illustrating an emission spectroscopy according to the aspect of the same Embodiment of the present invention.
Figure 4B:
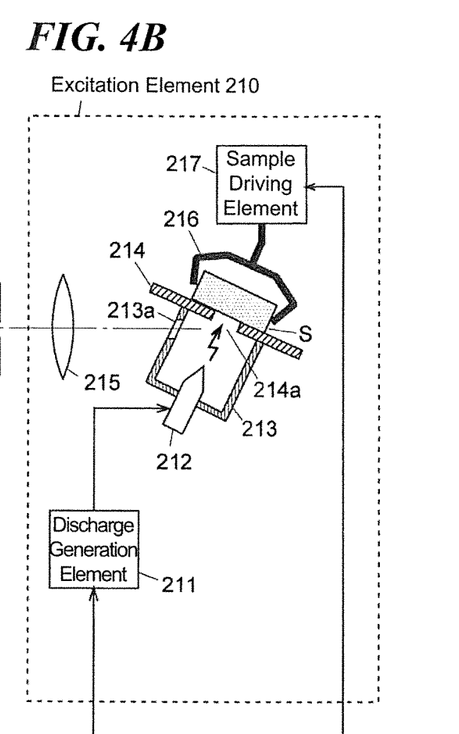
Figure 4C:
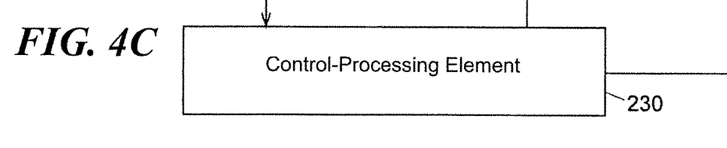
Figure 5:
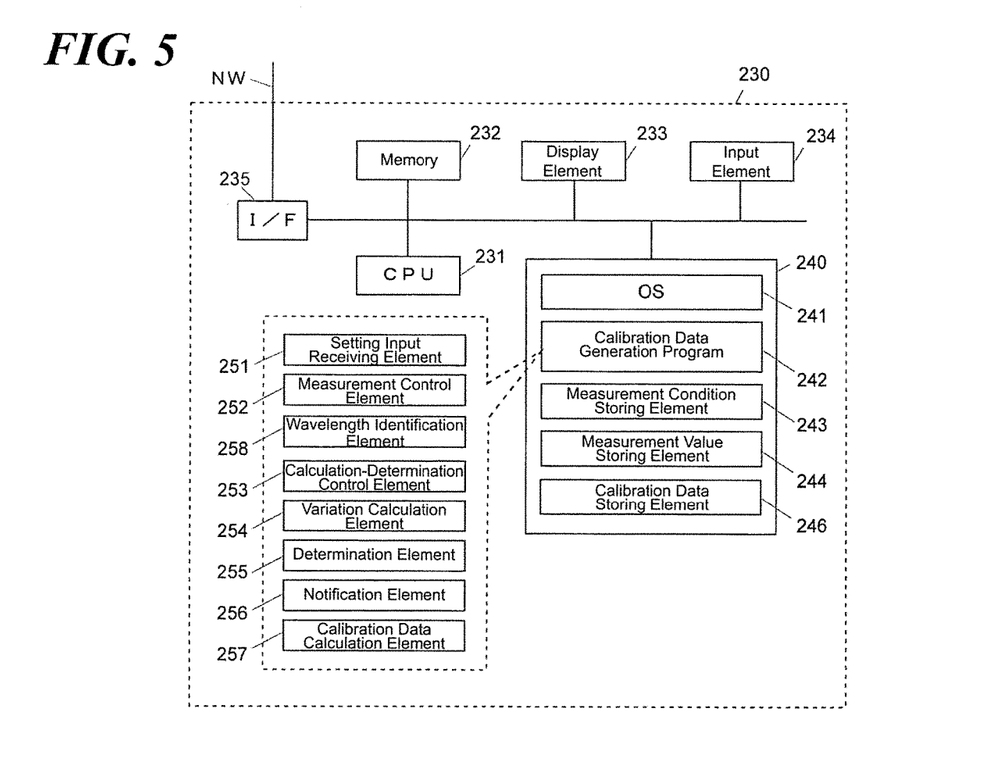
FIG. 5 is a block diagram illustrating a control and processing element according to the aspect of the same Embodiment.

FIGS. 4A-4C are schematic diagrams illustrating an emission spectroscopy according to the aspect of an alternative Embodiment of the present invention, and FIG. 5 is a block diagram illustrating a control and processing element according to the aspect of the same Embodiment. In addition, the aspect (element) as the same as or corresponding to FIGS. 1A-1C and FIG. 2 is given the sign having the same last two digits and the explanation may be skipped arbitrarily.

The spectroscopic element 220, according to the aspect of the present Embodiment 1, comprises a plurality (here, 3) of the multi-channel-type photodetectors 224a, 224b, 224c instead of the slit and the photoelectron multiplier. Such multi-channel-type photodetectors 224a, 224b, 224c are liner CCD sensors and any such sensor comprises a number of light receiving elements. Relative to the emission spectroscopy 220, the multi-channel-type photodetectors 224a, 224b, 224c detect lights having a predetermined wavelength range among the light that is incident from the excitation element 210 and then subjected to the wavelength dispersion at the diffraction grating 222 at once. In addition, the excitation element 210, according to the aspect of the present Embodiment, comprises a sample moving mechanism 216 that consists of such as a robot-arm and so forth to change the location of the sample S on the sample loading plate 214, and a sample driving element 217 to drive the sample moving mechanism 216.

In addition, according to the aspect of the present Embodiment, the control-processing element 230 comprises a setting input receiving element 251, a measurement control element 252, a variation calculation element 254, a determination element 255, a notification element 256, a calibration data calculation element 257, and a calculation-determination control element 253 that controls the variation calculation element 254 and the determination element 255 as a function block of the calibration data generation program 242 as well as the Embodiment 1, and a wavelength identification element 258 (set forth in detail later). In contrast, according to the aspect of the present Embodiment, the control-processing element 230 does not include the benchmark value storing element 145 according to the aspect of the Embodiment 1.

According to the aspect of the present Embodiment, with regard to the emission spectroscopy using multi-channel-type photodetectors 224a, 224b, 224c (hereinafter "detector 224a, 224b, 224c) to detect the spectral line, the distance between each structural element that consists of the spectroscopic element 220 changes due to such as temperature and so forth, so that an incident location of each spectral line on the light receiving surface of the detector 224a, 224b, 224c may shift. Specifically, a deviation of the corresponding relationship between each light receiving element that are arranged on the light receiving surface of the detector 224a, 224b, 224c and the light wavelength that the light receiving element detects occurs.

Figure 6:
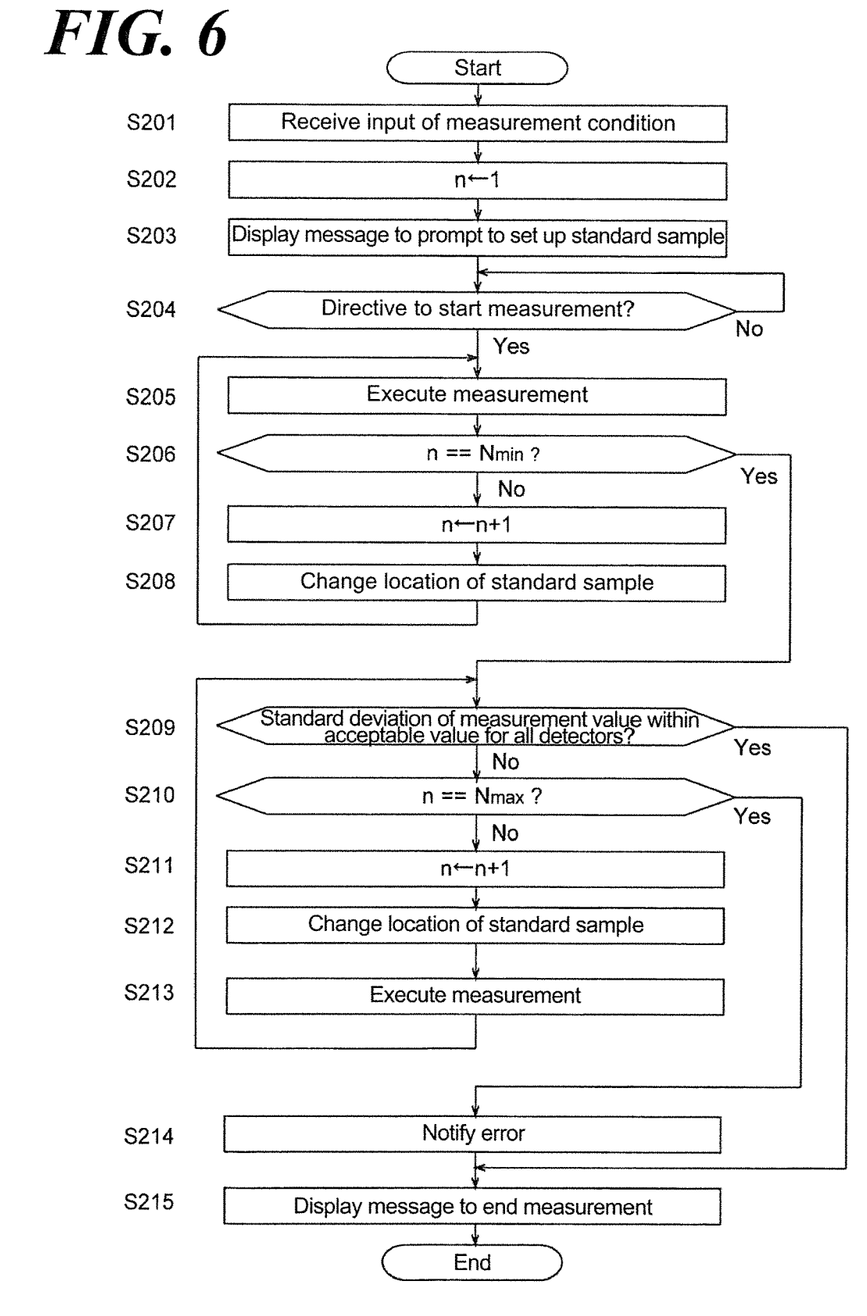
FIG. 6 is a flow-chart illustrating the measurement procedure of the standard sample for calibration according to the aspect of the Embodiment 2.

Therefore, according to the aspect of the present Embodiment, the emission spectroscopy measures the standard sample S for calibration when starting the device following the procedure illustrated by the flow-chart in FIG. 6, so that the corresponding relationship between each light receiving element and the detection wavelength can be calibrated.

First, once the operator starts the calibration data generation program 242 by executing the predetermined operating through the input element 234, the setting input receiving element 251 receives the input of a variety of measurement conditions (e.g., an acceptable value of variation of measurement values, the minimum measurement number $N_{min}$ and the maximum measurement number $N_{max}$) to measure the standard sample S (step S201). In addition, the inventor sets forth as the minimum measurement times $N_{min}$ is "3" and the maximum measurement times $N_{max}$ is "10" relative to the step S201. Once the operator completes to input the measurement conditions, the calibration data generation program 242 specifies the variable n as 1 (step S202) and displays the message on the display element 233 to prompt the operator setting up the standard sample S in the excitation element 110 (step S203).

Once the operator directs to start the measurement when the standard sample S containing the known concentration of the content is loaded on the sample loading plate 214, the measurement of the standard sample S is executed according to the control by the measurement control element 252 (steps S204, S205). Specifically, when the discharge from the electrode bar 212 vaporizes the standard sample S to excite to emit light, the emission light is induced into the spectroscopic element 220. The emitted light is subjected to the wavelength dispersion at the diffraction grating 222 and the light having the predetermined wavelength range are incident into the detector 224a, 224b, 224c at once. And the detection signal from a plurality of light receiving elements included in each detector 224a, 224b, 224c is sent to the control-processing element 230 via the A/D converter 225.

The control-processing element 230 identifies the incident location of the predetermined spectral line relative to the wavelength dispersion of the light receiving surface of each detector 224a, 224b, 224c by the wavelength identification element 258 based on the signal intensity relative to each light receiving element. The identification of such incident location is carried out relative to e.g., the two spectral lines that are incident into the location on the light receiving surface as much as far away relative to each detector 224a, 224b, 224c, and the incident locations of the total six spectral lines are stored in the measurement value storing element 244 as the measurement values. Once one measurement is completed, the calibration data generation program 242 determines whether the variable n is equal to the minimum measurement number $N_{min}$ or not (step S206).

And if the variable n is not equal to $N_{min}$, the variable n is incremented (step S107), and the measurement control element 252 controls the sample driving element 217 to change the location and the facing direction of the standard sample S on the sample loading plate 214 so that the region, not yet subjected to the measurement, of the bottom surface of the standard sample S is exposed from the central opening 214a (step S208). Then after, the step returns to the step S205 and the steps from the step S205 to the step S208 are repeatedly executed until the variable n becomes equal to the minimum measurement number $N_{min}$.

Then after, when it is determined that the variable n is equal to the minimum measurement number $N_{min}$ (here, "3") at the step S206, whether the standard deviation of the measurement values of the light receiving intensities obtained by the update measurement is within the acceptable value or not is determined (step S209). Specifically, firstly, the measurement values of the incident locations of each two spectral lines of the three measurements of the standard sample S relative to each detector 224a, 224b, 224c are read out from the measurement value storing element 244, and the variation calculation element 254 calculates the standard deviation of such measurement values every spectral line. Next, the determination element 255 determines whether the standard deviation value is within the acceptable value relative to all spectral lines (here, 6 spectral lines) subjected to the measurement, i.e., the standard deviation of the measurement values is within the acceptable value relative to all detectors 224a, 224b, 224c or not.

And when all standard deviation of the measurement values relative to the detectors 224a, 224b, 224c are within the acceptable value, the notification element 256 displays the message denoting the completion of the measurement on the display element 233 (step S215) followed by the end of the measurement of the standard sample S.

On the other hand, when the standard deviation of the measurement values relative to any one of the detectors 224a, 224b, 224c is out of the acceptable value at the step S209, the calibration data generation program 242 determines whether the variable n is equal to the minimum measurement number $N_{max}$ or not (step S210). And if the variable n is not equal to $N_{max}$, the variable n is incremented (step S211), and subsequently, the sample driving element 217 changes at least one of the location and the facing direction of the standard sample S followed by execution of the measurement again (steps S212, S213).

Then after, the step returns to the step S209 every time when the standard sample is measured once and the variation calculation element 254 calculates the standard deviation and in addition, the determination element 255 determines whether the standard deviation is within the acceptable value or not. And the steps from the step S209 to the step S213 are repeatedly executed until when it is determined that the standard deviations of the measurement values relative to all detectors 224a, 224b, 224c are within the acceptable value at the step S209 or until when the variable n is equal to the maximum measurement number $N_{max}$ at the step S210.

In addition, relative to the step S209, the variation calculation element 254 and the determination element 255 select the predetermined number. e.g., three, of measurement values from a plurality of measurement values obtained by that time to make the standard deviation thereof minimum by combination thereof and apply such standard deviation obtained by such combination to the determination. Specifically, when relative to any detector (any one of detectors 224a, 224b, 224c), the standard deviations relative to any three measurement values of each n measurement values obtained from the first measurement to the nth (i.e., update) measurement relative to the two spectral lines as the detection target are within the acceptable value, it is determined that the standard deviation of the measurement values relative to such detectors is within the acceptable value. In addition, the number of the selected measurement values is typically the same as the minimum measurement number $N_{min}$, but not limited thereto and any number more than 2 and less than n (the measurement number at that time) can be applied.

And the step proceeds to the step S215 when the standard deviation of the measurement values relative to the detectors 224a, 224b, 224c is within the acceptable value, the message denoting the completion of the measurement is displayed on the display element 233 followed by the end of the measurement of the standard sample S.

In addition, when it is determined that the variable n is equal to the maximum measurement number $N_{max}$ at the step S210 (i.e., the standard sample S is measured 10 times), the notification element 256 displays the message denoting the calibration error and ending the measurement on the display element 233 (steps S214, S215) and then the measurement of the standard sample S ends.

As set forth above, once the measurement of the standard sample S ends normally (i.e., end with no calibration error), the calibration data relative to the detectors are generated from the measurement values of the incident locations of the two spectral lines obtained by the measurement of the standard sample S relative to the detectors 224a, 224b, 224c. Specifically, the content of the standard sample S is known, so that the wavelength of each spectral line generated from the standard sample S is also known. Therefore, given the incident locations of each two spectral lines in the wavelength dispersion direction on the light receiving surface of the detector 224a, 224b, 224c are determined, the light wavelength incident to the other location in the wavelength dispersion direction on the light receiving surface can be obtained by the linear interpolation. Specifically, the corresponding relationship between each light receiving element included in each detector 224a, 224b, 224c and the light wavelength that the light receiving element detects can be obtained using the measurement values of the standard sample. Such data relative to the corresponding relationship are stored in the calibration data storing element 246 as the wavelength calibration data and are applied to the following measurement.

In addition, here, the incident locations of the two spectral lines relative to each detector 224a, 224b, 224c are measured, but more than three spectral lines can be respectively measured. In such case, the more accurate wavelength calibration can be achieved by a curve interpolation of the measurement values of the incident locations of more than three spectral lines.

In addition, according to the aspect of the present Embodiment, the emission spectroscopy can apply the sensitivity calibration as well as the aspect of the Embodiment 1 in addition to the above wavelength calibration. In such case, for example, it is determined that the standard deviations of the measurement values relative to not only the incident location of the predetermined spectral lines at the step S209 but also the light receiving intensity of the spectral lines are within the acceptable value, and consequently, once both the standard deviations of the measurement values of the incident locations and the standard deviations of the measurement values of the light receiving intensity relative to all detectors are respectively within the acceptable value, the measurement of the standard sample S ends.

As set forth above, the inventor sets forth the specific embodiments according to the aspect of the present invention, but the present invention is not limited thereto, and the present invention can be arbitrarily modified within the scope of the spirit of the present invention.

For example, according to the aspect of the present Embodiment, the emission spectroscopy of the present invention is a solid emission spectroscopy instrumentation that excites the solid sample to emit light by discharge and measures the emission light by the spectroscope, but the present invention is not limited thereto, and, for example, the aspect of the present invention can be also applied to an inductively coupled plasma (ICP) emission spectroscopy instrumentation that excites a liquid sample or a gas sample by the high-temperature plasma to emit light and measures the emission lights by the spectroscope.

REFERENCE OF SIGNS 110, 210 Excitation element
111, 211 Discharge generation element
112, 212 Electrode bar
113, 213 Discharge chamber
114, 214 Sample loading plate
216 Sample moving mechanism
217 Sample driving element
120, 220 Spectroscopic element
121, 221 Entrance slit 122, 222 Diffraction grating
123a, 123b, 123c Exit slit
124a, 124b, 124c Detector
224a, 224b, 224c Multi-channel-type photodetector
130, 230 Control-processing element
133, 233 Display element
134, 234 Input element
140, 240 Memory element
142, 242 Calibration data generation program
143, 243 Measurement condition storing element
144, 244 Measurement value storing element
145 Benchmark value storing element
146, 246 Calibration data storing element
151, 251 Setting input receiving element
152, 252 Measurement control element
153, 253 Calculation-determination control element
154, 254 Variation calculation element
155, 255 Determination element
156, 256 Notification element
157, 257 Calibration data calculation element
258 Wavelength identification element As used herein, a computer-involved system includes an input device for receiving data in any form, an output device for outputting data in any form (e.g. data stream, stored electrons, visual, sound, print, or displaying on a computer screen and any others), a memory for storing data as well as any code of any form, a processor for executing computer code wherein said computer code is resident in said permanent memory will cause said microprocessor to read-in data via said input device, process said data within said microprocessor and output said processed data via said output device.

It will be further understood by those of skill in the art that the apparatus and devices and the elements herein, without limitation, and including the sub components such as operational structures, operational elements, circuits, communication pathway ys, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related emission spectrographic instruments and devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, logic elements, circuits, and steps have been described above generally in terms of their functionality. Whether such functionality is implemented as hardware or software depends upon the particular application and design constraints imposed on the overall system. Skilled artisans at this level of technology may implement the described functionality in varying ways for each particular application within the scope and skill in the art, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm in any form described in connection with the embodiments disclosed herein may be embodied directly in hardware, in a software module executed by a processor, using cloud computing, or in any combinations thereof. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An emission spectroscopy instrumentation, comprising:
an emission spectroscopy that excites a standard sample by providing an energy to emit light and detects a plurality of spectral lines obtained by a wavelength dispersion of an emission light by a plurality of detectors,
and further comprising:
(a) a calculator comprising a processor configured to execute processor-executable instructions for calculating a variation of a plurality measurement values obtained by a plurality of measurements of the standard sample relative to each of said plurality of the detectors;
(b) a determiner comprising a processor configured to execute processor-executable instructions for determining that no additional measurement is required when said variation relative to all of said plurality of detectors is within a predetermined acceptable value and an additional measurement is required when said variation relative to at least one of said plurality of detectors is out of said predetermined acceptable value;
(c) a notifier comprising a processor configured to execute processor-executable instructions for notifying a determination result by said determiner to an external operator;
(d) a controller comprising a processor configured to execute processor-executable instructions for controlling said calculator and said determiner so that said calculator calculates said variation and said determiner determines at a timing when a measurement of said standard sample is carried out a predetermined number of times, and when said determiner determines that an additional measurement is required, and said calculator calculates a variation and said determiner determines every time when one additional measurement is carried out.

2. The emission spectroscopy instrumentation, according to claim 1, further comprising:
an additional measurement executer comprising a processor configured to execute processor-executable instructions for executing an additional measurement of a standard sample when said determiner determines that an additional measurement of said standard sample is needed, and wherein said additional measurement executer is operative to replace said notifier.

3. The emission spectroscopy instrumentation, according to claim 2, wherein:
said calculator calculates said variation based on said measurement values of a predetermined number among said measurement values that are obtained by multiple measurements of said standard sample and selects said predetermined number of measurement values to make said variation value to be minimum.

4. The wavelength conversion device according to claim 3, wherein:
said measurement value is at least one of a light receiving intensity relative to said detector and a calibration coefficient calculated from said light receiving intensity.

5. The emission spectroscopy instrumentation, according to claim 4, wherein:
said determiner determines that a calibration is erroneous when said variation relative to at least one of said plurality of detectors is out of said acceptable value even when a measurement of said standard sample is executed over a predetermined maximum number of times.

6. The emission spectroscopy instrumentation, according to claim 3, wherein:
said detector is a multi-channel-type photodetector and said measurement value is an incident location of a predetermined spectral line on a light receiving surface of said multi-channel-type detector.

7. The emission spectroscopy instrumentation, according to claim 3, wherein:
said determiner determines that a calibration is erroneous when said variation relative to at least one of said plurality of detectors is out of said acceptable value even when a measurement of said standard sample is executed over a predetermined maximum number of times.

8. The emission spectroscopy instrumentation, according to claim 2, wherein:
said measurement value is at least one of a light receiving intensity relative to said detector and a calibration coefficient calculated from said light receiving intensity.

9. The emission spectroscopy instrumentation, according to claim 8, wherein:
said determiner determines that a calibration is erroneous when said variation relative to at least one of said plurality of detectors is out of said acceptable value even when a measurement of said standard sample is executed over a predetermined maximum number of times.

10. The emission spectroscopy instrumentation, according to claim 2, wherein:
said detector is a multi-channel-type photodetector and said measurement value is an incident location of a predetermined spectral line on a light receiving surface of said multi-channel-type detector.

11. The emission spectroscopy instrumentation, according to claim 2, wherein:
said determiner determines that a calibration is erroneous when said variation relative to at least one of said plurality of detectors is out of said acceptable value even when a measurement of said standard sample is executed over a predetermined maximum number of times.

12. The emission spectroscopy instrumentation, according to claim 1, wherein:
said calculator calculates said variation based on measurement values of a predetermined number among said measurement values that are obtained by multiple measurements of said standard sample and selects said predetermined number of measurement values to make said variation value to be minimum.

13. The emission spectroscopy instrumentation, according to claim 12, wherein:
said measurement value is at least one of a light receiving intensity relative to said detector and a calibration coefficient calculated from said light receiving intensity.

14. The emission spectroscopy instrumentation, according to claim 13, wherein:
said determiner determines that a calibration is erroneous when said variation relative to at least one of said plurality of detectors is out of said acceptable value even when a measurement of said standard sample is executed over a predetermined maximum number of times.

15. The emission spectroscopy instrumentation, according to claim 12, wherein:
said detector is a multi-channel-type photodetector and said measurement value is an incident location of a predetermined spectral line on a light receiving surface of said multi-channel-type detector.

16. The emission spectroscopy instrumentation, according to claim 12, wherein:
said determiner determines that a calibration is erroneous when said variation relative to at least one of said plurality of detectors is out of said acceptable value even when a measurement of said standard sample is executed over a predetermined maximum number of times.

17. The emission spectroscopy instrumentation, according to claim 1, wherein:
said measurement value is at least one of a light receiving intensity relative to said detector and a calibration coefficient calculated from said light receiving intensity.

18. The emission spectroscopy instrumentation, according to claim 17, wherein:
said determiner determines that a calibration is erroneous when said variation relative to at least one of said plurality of detectors is out of said acceptable value even when a measurement of said standard sample is executed over a predetermined maximum number of times.

19. The emission spectroscopy instrumentation, according to claim 1, wherein:
said detector is a multi-channel-type photodetector and said measurement value is an incident location of a predetermined spectral line on a light receiving surface of said multi-channel-type detector.

20. The emission spectroscopy instrumentation, according to claim 1, wherein:
said determiner determines that a calibration is erroneous when said variation relative to at least one of said plurality of detectors is out of said predetermined acceptable value even when a measurement of said standard sample is executed over a predetermined maximum number of times.

* * * * *